United States Patent
Bharat et al.

(10) Patent No.: US 10,737,116 B2
(45) Date of Patent: Aug. 11, 2020

(54) THERAPY PLANNING

(71) Applicants: KONINKLIJKE PHILIPS N.V., Eindhoven (NL); THE UNIVERSITY OF TEXAS SOUTHWESTERN MEDICAL CENTER AT DALLAS, Dallas, TX (US)

(72) Inventors: Shyam Bharat, Arlington, MA (US); Sankara Hari Gopalakrishnan, Madison, WI (US); Amit Ramakant Sawant, Richardson, TX (US)

(73) Assignees: KONINKLIJKE PHILIPS N.V., Eindhoven (NL); BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 876 days.

(21) Appl. No.: 14/910,008

(22) PCT Filed: Jul. 29, 2014

(86) PCT No.: PCT/IB2014/063501
§ 371 (c)(1),
(2) Date: Feb. 4, 2016

(87) PCT Pub. No.: WO2015/019241
PCT Pub. Date: Feb. 12, 2015

(65) Prior Publication Data
US 2016/0166854 A1   Jun. 16, 2016

Related U.S. Application Data

(60) Provisional application No. 61/862,979, filed on Aug. 7, 2013.

(51) Int. Cl.
*A61N 5/10* (2006.01)

(52) U.S. Cl.
CPC ......... *A61N 5/1037* (2013.01); *A61N 5/1039* (2013.01); *A61N 5/1067* (2013.01)

(58) Field of Classification Search
CPC .................. A61N 5/1037–1039; A61N 5/1067
See application file for complete search history.

(56) References Cited

U.S. PATENT DOCUMENTS

| | | | |
|---|---|---|---|
| 2006/0074292 A1 | 4/2006 | Thomson et al. | |
| 2007/0076846 A1* | 4/2007 | Ruchala | A61N 5/103 378/65 |

(Continued)

FOREIGN PATENT DOCUMENTS

| | | |
|---|---|---|
| EP | 2532386 | 12/2012 |
| WO | 2013024380 | 2/2013 |
| WO | 2013080175 | 6/2013 |

OTHER PUBLICATIONS

Men, et al., "An efficient approach to incorporating interfraction motion in IMRT treatment planning", Computers & Operations Research 39 (2012) 1779-1789.

*Primary Examiner* — Thaddeus B Cox

(57) ABSTRACT

When reducing radiation dose to healthy tissue near a target volume, a 4D motion model (52) of a target volume is generated during CT scan data acquisition. The target volume is tracked, and tracked target volume position information (43) is provided to a motion estimation tool (48). Motion parameter information (60) output from the motion estimation tool is linked to motion phases of the target volume indicated by CT scan data. A dynamic planned target volume (PTV) (64) that covers the target volume in each motion phase is generated and linked to tracked motion parameters for each respective motion phase. A radiation dose is delivered to the PTV for each motion phase using the linked motion parameters and real-time tracking information.

20 Claims, 5 Drawing Sheets

(56) References Cited

U.S. PATENT DOCUMENTS

2007/0201613 A1    8/2007  Lu
2013/0211261 A1*  8/2013  Wang ..................... A61B 5/055
                                                          600/476

* cited by examiner

THERAPY PLANNING

CROSS REFERENCE TO RELATED APPLICATIONS

This application is the U.S. National Phase application under 35 U.S.C. § 371 of International Application No. PCT/IB2014/063501, filed Jul. 29, 2014, published as WO 2015/019241 on Feb. 12, 2015, which claims the benefit of U.S. Provisional Patent Application No. 61/862,979 filed Aug. 7, 2013. These applications are hereby incorporated by reference herein.

The present innovation finds particular application in radiation therapy systems. However, it will be appreciated that the described techniques may also find application in other therapy systems, other radiation dose control scenarios, or other radiation dose delivery techniques.

Radiation treatment is often applied to tumors that move as the patient breathes. Conventionally, the target volume is defined during radiation therapy planning such that the target is covered in all motion phases. This approach irradiates a significant amount of healthy tissue. For instance, generic population-based margins can be utilized to ensure target dosage in the presence of motion. Therefore, normal tissue surrounding the target may receive unnecessary dose, leading to poor patient outcomes and reduced quality-of-life after treatment. Traditional static planning target volumes (PTV) are created so as to encompass all quantified positions of the target (e.g., as determined from CT scans or the like). Thus, at any given point in time during conventional treatment delivery, a significant amount of normal tissue receives unnecessary dose.

Treatment planning in external beam radiation therapy (EBRT) is traditionally a one-time process, following which treatment is delivered over multiple fractions. Some systems provide functionality that uses real-time tracking information from the target and estimates one or more motion parameters to quantify this motion. Target motion between and during these treatment delivery fractions hinders the ability to deliver the treatment as planned.

The present application relates to new and improved systems and methods that overcome the problems of irradiating healthy tissue and patient motion during treatment by providing real-time target volume tracking, which overcome the above-referenced problems and others.

In accordance with one aspect, a method of reducing radiation dose to healthy tissue near a target volume comprises generating a dynamic planned target volume (PTV) for each of a plurality of motion phases of the target volume identified in a 4D motion model generated by tracking motion of a target volume during computed tomography (CT) data acquisition, wherein the motion phases are identified from one or more CT images reconstructed from acquired CT data. Additionally, the method comprises, during a treatment stage, tracking the target volume; and at each motion phase of the target volume, selecting a dynamic PTV corresponding to the motion phase to cover the target volume, and outputting instructions for irradiating the selected dynamic PTV at each motion phase of the target volume.

According to another aspect, a therapy planning system that facilitates reducing radiation dose to healthy tissue near a target volume comprises a tracking module that tracks target volume motion using one or more 4D computed tomography (CT) images reconstructed from acquired CT scan data of the target volume. The system further comprises a processor configured to generate a 4D motion model for the target volume using tracking information generated by the tracking module, and to generate a dynamic planned target volume (PTV) for each of a plurality of motion phases of the target volume identified in the motion model. Additionally, the system comprises a motion estimation tool configured to track the target volume. The processor is further configured to, at each motion phase of the target volume, select a dynamic PTV corresponding to the motion phase to cover the target volume, and output instructions for irradiating the selected dynamic PTV at each motion phase of the target volume.

According to another aspect, a method of reducing radiation dose to healthy tissue near a target volume comprises providing tracked target volume position information from a 4D motion model of the target volume to a motion estimation tool, and linking motion parameter information output from the motion estimation tool to motion phases of the target volume indicated by CT scan data. The method further comprises generating a dynamic planned target volume (PTV) that covers the target volume in each motion phase, linking the dynamic PTV for each motion phase to tracked motion parameters for each respective motion phase, and outputting instructions for irradiating the PTV for each motion phase.

One advantage is that radiation dose to healthy tissue is reduced.

Another advantage is that desired radiation dose to the target volume is achieved.

Still further advantages of the subject innovation will be appreciated by those of ordinary skill in the art upon reading and understanding the following detailed description.

The innovation may take form in various components and arrangements of components, and in various steps and arrangements of steps. The drawings are only for purposes of illustrating various aspects and are not to be construed as limiting the invention.

The subject innovation overcomes the aforementioned problem of undesirable irradiation of healthy tissue near a target volume by employing real-time target volume tracking using a map of target location versus motion state. During the radiation therapy planning, a target volume is defined for each motion state. During therapy, patient movement is tracked and the current motion state is determined.

Using a look-up table or the like, the therapy plan for a current motion phase is determined. A radiation source control module steers the therapy beam by controlling a collimator positioned between the radiation source and the patient, and a dose module modulates the beam to control the dose as indicated by the treatment plan for the current motion phase. As used herein, "target volume" denotes a tumor or mass to be irradiated (or ablated, treated using particle therapy, or any other suitable therapy type), and "planned target volume" or "PTV" denotes a volume that covers or encompasses the target volume. Although systems and methods are described herein with regard to radiation therapy planning and the like, it will be appreciated by those of skill in the art that such systems and methods are also applicable to other therapy types, including without limitation ablation therapy, particle therapy, or any other suitable type of therapy.

Figure 1:
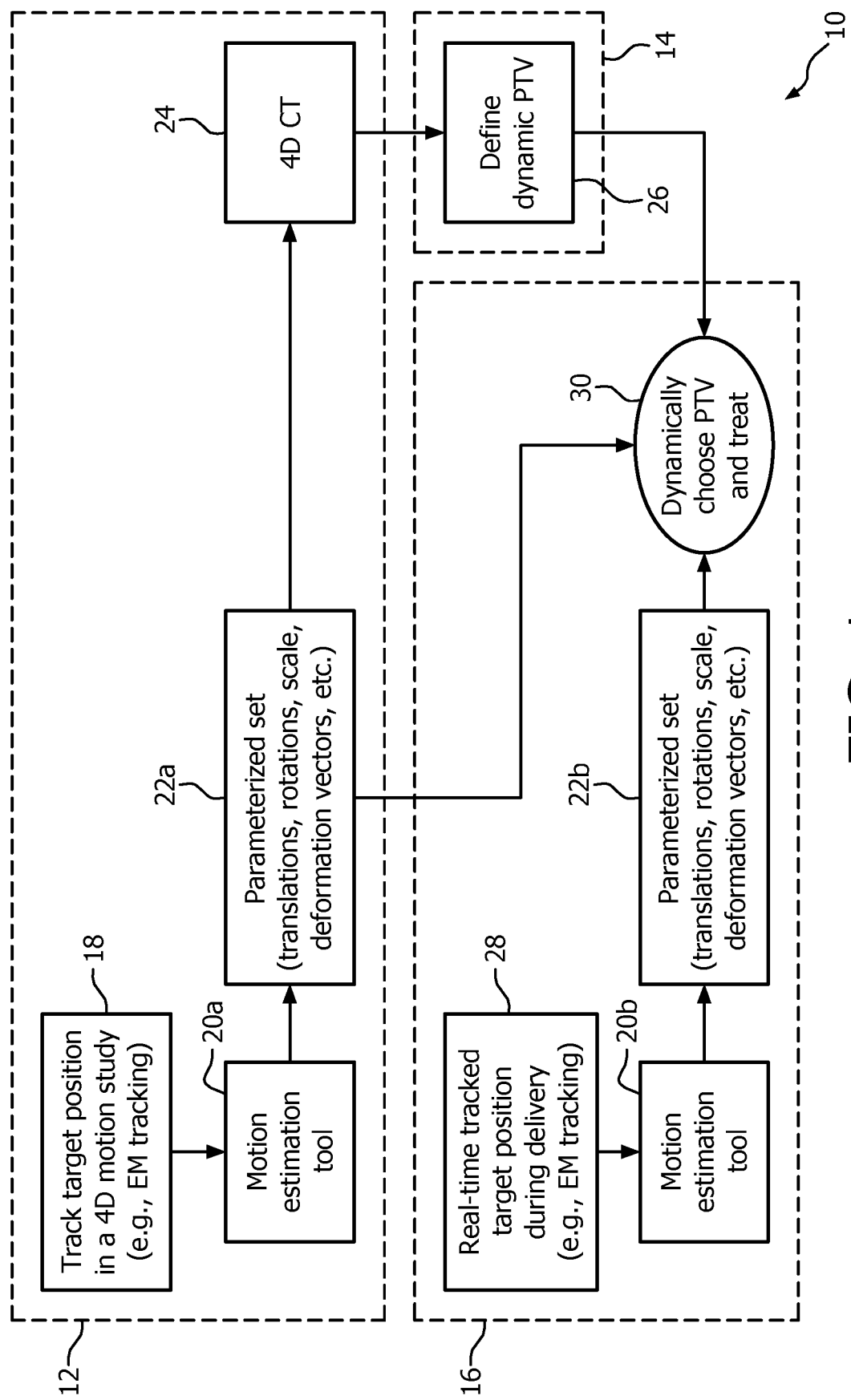
FIG. 1 illustrates a workflow for reducing radiation dose to healthy tissue during external beam radiation therapy (EBRT), in accordance with one or more aspects described herein.

FIG. 1 illustrates a workflow 10 for reducing radiation dose to healthy tissue during external beam radiation therapy (EBRT), in accordance with one or more aspects described herein. The workflow comprises three main stages, including a simulation stage 12, a treatment planning stage and 14, and a delivery stage 16. The simulation stage 12 comprises a tracking step 18 in which target (e.g. a tumor or the like) position is tracked in a 4D motion study. In one embodiment, electromagnetic (EM) tracking is performed at 18. A motion estimation tool 20a (e.g. a delivered dose investigational tool (DiDIT) such as is provided in Philips' Pinnacle$^3$ system or the like) is employed to generate a parameterized set of data 22a that includes, e.g., translations, rotations, scale, deformation vectors, etc., of the target volume during motion. A 4D computed tomography (CT) scanner 24 employs the parameterized set data 22a, and, in the treatment planning stage 14, a dynamic planned target volume (PTV) is defined, at 26. In the treatment delivery stage 16, target volume tracking is performed in real-time to track a target position during radiation delivery, at 28. In one embodiment, EM tracking is employed to track the target volume. A motion estimation tool 20b is employed to generate parameterized set data 22b. Motion estimation tool 20b may be similar or identical to the motion estimation tool 20a. At 30, a PTV is dynamically chosen and treated based on the parameterized set data 22a, the parameterized set data 22b, and the dynamic PTV defined at 26. In this manner, in contrast to conventional approaches that irradiate an entire volume traversed by the moving PTV, the described workflow 10 facilitates irradiating the moving PTV at a plurality of different PTV locations, in order to minimize radiation dose to healthy tissue surrounding the PTV.

It will be appreciated that the DiDIT motion estimation tool described herein is provided by way of example, and that the described systems and methods are not limited thereto. The described motion estimation tool 20a, 20b can be utilized prospectively (during simulation) and during treatment delivery to parameterize target motion, as well as retrospectively.

Figure 2:
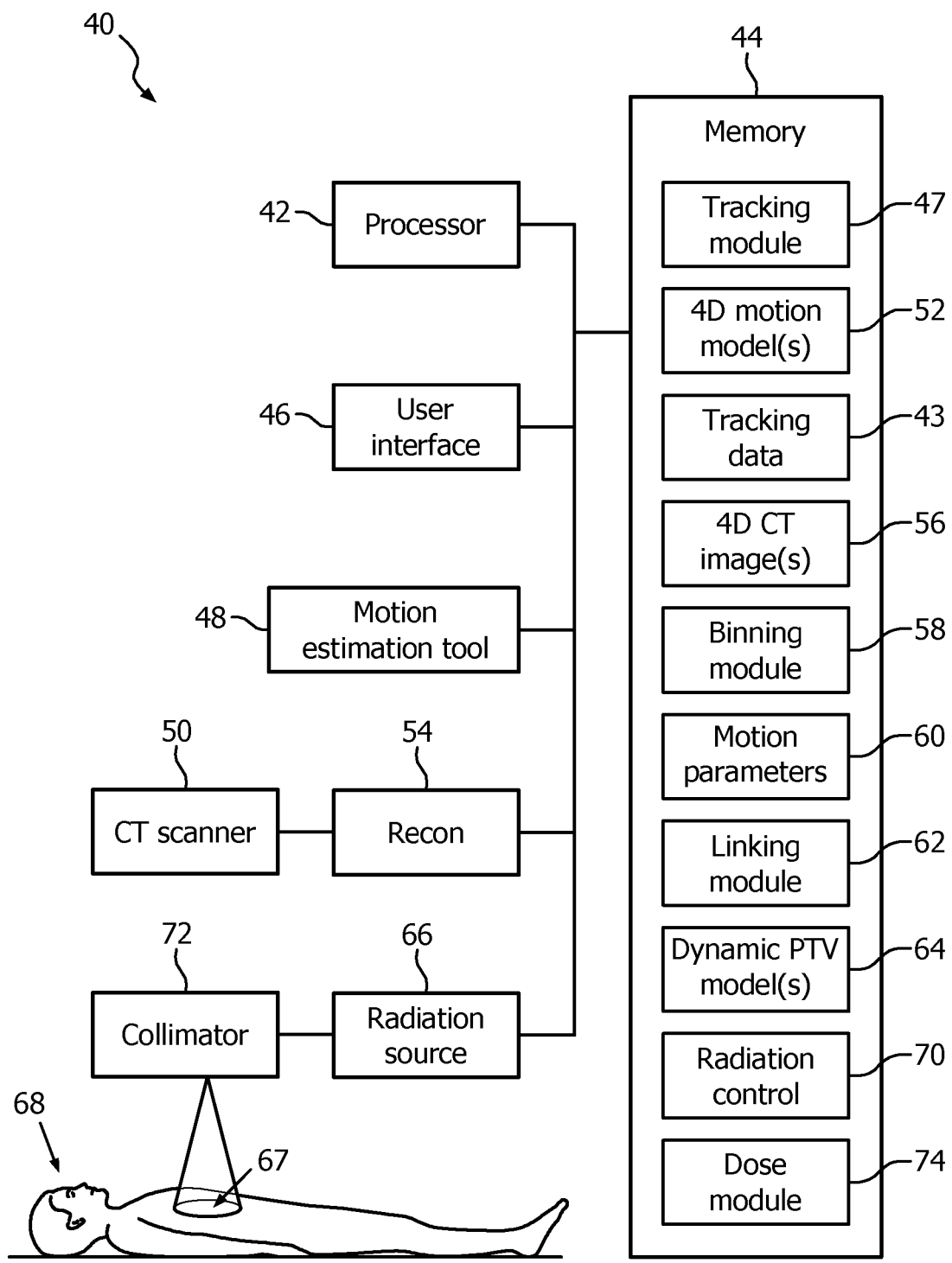
FIG. 2 illustrates a system that facilitates reducing radiation dose to normal tissue in accordance with one or more aspects described herein.

FIG. 2 illustrates a system 40 that facilitates reducing radiation dose to normal tissue in accordance with one or more aspects described herein. The system includes a processor 42 operably coupled to a memory 44 and a user interface 46. The processor 42 executes, and the memory 44 stores, computer-executable instructions (e.g., routines, programs, algorithms, software code, modules, etc.) for performing the various functions, methods, procedures, etc., described herein. Additionally, "module," as used herein, denotes a set of computer-executable instructions, software code, program, routine, or other computer-executable means for performing the described function, or the like, which is stored on a computer-readable medium and/or executed by one or more processors, as will be understood by those of skill in the art.

The memory may be a computer-readable medium on which a control program is stored, such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor can read and execute. In this context, the systems described herein may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like.

The system 40 further includes a tracking module 47 that tracks target volume position during the CT scan, and a motion estimation tool 48 in the CT scanner 50. The processor 42 generates a 4D motion model 52 of a target volume (e.g. a tumor or the like) in a patient during simulation, using motion tracking data 53 generated by the tracking module 47. Examples of tracking technologies employed by the motion estimation tool include but are not limited to implanted wireless electromagnetic (EM) trackers, surface tracking (using optical shape sensing or high frequency video cameras), external fiducial tracking (using high frequency video cameras), internal anatomical marker tracking (using continuous fluoroscopy) etc. A reconstruction processor 54 reconstructs CT scan data acquired by the CT scanner 50 into 4D CT images 56 of the target volume (the 4$^{th}$ dimension being time). The processor executes a binning module 58 that bins the 4D CT images into N motion phases or positions, where N is an integer. The motion estimation tool 48 (e.g., DiDIT or any other suitable motion estimation tool) computes motion parameters 60 (e.g., translations, rotations, scale factors, deformable vector fields, etc., of the target volume and/or PTP therefore) for each tracked position of the target volume.

The processor executes a linking module 62 that links the motion parameters to a particular phase or position N of the target volume in the 4D CT dataset. This can be performed using timing information from the recorded tracking data and CT images 56. Other registration techniques can also be used, such as registering the tracking data waveform to an estimate of target motion obtained from CT image analysis. In one embodiment, the 4D motion model 52 is populated by monitoring the patient for an extended period of time during simulation, thereby capturing a large number of data points. During this process, the patient can be made to perform out-of-the-ordinary tasks (e.g. coughing, deep breathing, shallow breathing etc.) that are rare but may occur during therapy delivery.

The processor generates one or more dynamic PTV models 64, during the treatment planning stage. In one embodiment, each set of motion parameter outputs 60 from the motion estimation tool is linked by the linking module 62 to a unique phase or position of the 4D CT dataset (one-to-one mapping). In this case, each output set of the motion estimation tool is assigned a unique PTV 64 that is drawn on the corresponding phase in the 4D CT dataset (see, e.g., FIG.

5). This approach employs a temporally-dense 4D CT data set. In another embodiment, multiple sets of outputs from the motion estimation tool are linked by the linking module 62 to a given phase in the 4D CT dataset (many-to-one mapping). In this case, multiple motion parameter output sets of the motion estimation tool are assigned a common PTV that is drawn on the phase of the 4D CT dataset to which those outputs correspond (see, e.g., FIG. 6). Under this approach, the 4D CT dataset can be relatively sparse (e.g., 10 phases or some other predetermined number of phases). Although the 4D data set described herein as being generated from CT scan data and/or images, it will be appreciated that any suitable imaging modality can be employed in conjunction with the described therapy planning systems and methods, including but not limited to, e.g., ultrasound, magnetic resonance (MR) nuclear imaging modalities such as positron emission tomography (PET), single photon emission computed tomography (SPECT), x-ray, xCT, variants of the foregoing, etc.

During a treatment delivery stage, a radiation source 66 (e.g., a linear accelerator or the like) is provided with instructions to deliver a radiation dose to a dynamically-changing PTV 67 in a patient 68 using real-time tracking information provided by the motion estimation tool 48 during radiation dose delivery. In one example, the tracking modality used during the simulation phase is also utilized continuously during treatment delivery (e.g., EM tracking, fluoroscopic movies, etc.). The 4D motion model 52 created during simulation and information related to the dynamic PTV models 64 generated during the treatment planning stage are used to determine which PTV margins to use at which time or phase, based on the real-time analysis of the incoming tracking data in the motion estimation tool. The radiation control module 70 is executed by the processor and employs one or more motion prediction algorithms to determine multi leaf collimator (MLC) leaf positions and control the collimator 72 during dose delivery in order to irradiate the PTV at each phase of target volume motion while reducing radiation dose to healthy tissue near the target phone. Additionally, a dose module 74 can be executed by the processor to modulate the radiation source beam to further control radiation dose. For example, if a patient coughs during treatment delivery, the target volume will deviate from its normal path: the 4D motion model can be used to estimate the positions that will be traversed by the target volume to return to its "normal" or expected path. Based on this information, the appropriate PTV is chosen in advance for those time instants, and the collimator 72 is controlled to deliver radiation to the position of the PTV at a given instant.

In this manner, the described systems and methods reduce dose to normal tissue, using real-time tracking during simulation and treatment delivery. The described approach can be implemented in Pinnacle³, for instance using motion estimation functionality of Pinnacle³ (DiDIT). Real-time tracking may be achieved using electromagnetic (EM) tracking, optical shape sensing (OSS) of the external body surface, high frequency video cameras etc., none of which exposes the patient to additional radiation dose.

Figure 3:
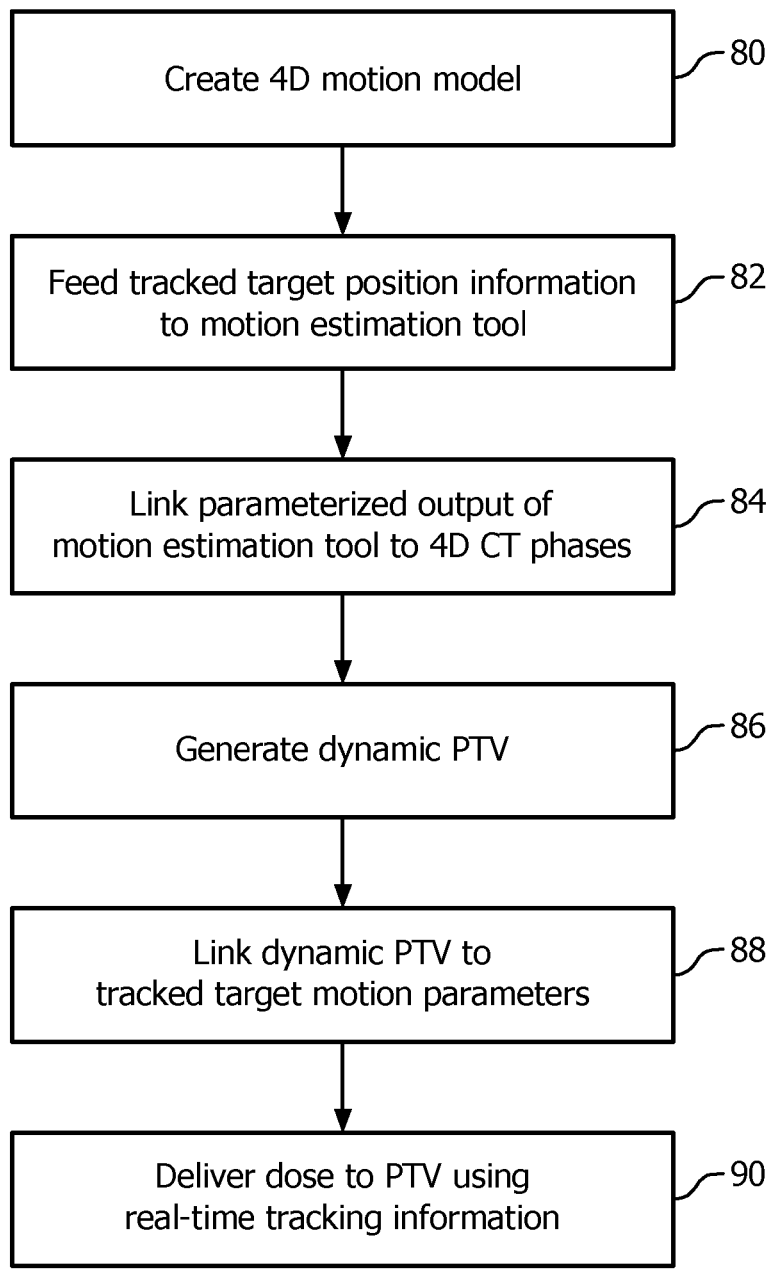
FIG. 3 illustrates a method for reducing dose to normal tissue surrounding a planned target volume, in accordance with one or more aspects described herein.

With continued reference to FIGS. 1 and 2, FIG. 3 illustrates a method for reducing dose to normal tissue surrounding a planned target volume, in accordance with one or more aspects described herein. The method can be executed by a computer and/or the processor 42 (FIG. 2), in conjunction with the memory 44 (FIG. 2) and user interface 46 (FIG. 2), and/or any other suitable components of FIGS. 1 and/or 2.

At 80, a 4D motion model is created for the target during a simulation phase using tracking technology and 4D CT images. The tracked target positions are fed to a motion estimation tool (e.g., Pinnacle³'s DiDIT, which parameterizes target positions in terms of translations and rotations relative to a reference position), at 82. The parameterized output of the motion estimation tool is linked to the 4D CT phases, at 84. A dynamic PTV is generated during treatment planning, at 86. For instance, a dynamic PTV is created on each of the 4D CT phases. At 88, the dynamic PTV is linked to the tracked target motion parameters, based on the 4D motion model created at 80, and an irradiation plan (e.g., computer-executable instructions or the like) is output, e.g., to a radiation source controller or the like. At 90, a radiation dose is delivered to the dynamic PTV using real-time tracking information during delivery. Real-time tracking of the target and the 4D CT motion model are utilized to determine which PTV to use as a function of delivery time.

Figure 4:
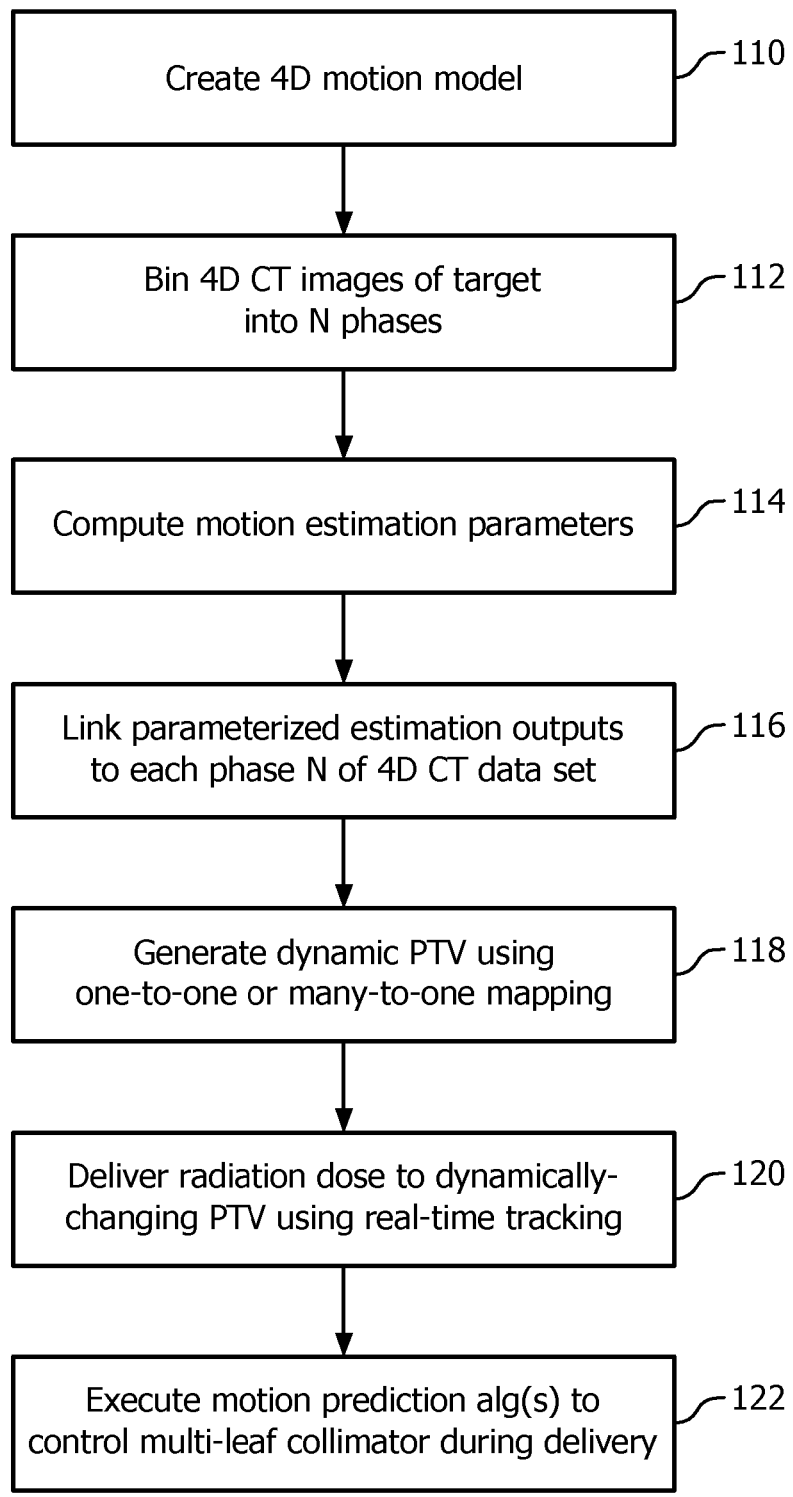
FIG. 4 illustrates a method for reducing radiation dose to normal tissue is accomplished by a novel method/workflow that transcends simulation, treatment planning and treatment delivery, in accordance with one or more aspects described herein.

FIG. 4 illustrates a method for reducing radiation dose to normal tissue, accomplished by a novel method/workflow that transcends simulation, treatment planning and treatment delivery, in accordance with one or more aspects described herein. The method can be executed by a computer and/or the processor 42 (FIG. 2), in conjunction with the memory 44 (FIG. 2) and user interface 46 (FIG. 2), and/or any other suitable components of FIGS. 1 and/or 2.

At 110, a 4D motion model is created for the target volume (e.g., a tumor or lesion or the like) during simulation, using motion tracking. Examples of tracking technologies include but are not limited to implanted wireless electromagnetic (EM) trackers, surface tracking (using optical shape sensing or high frequency video cameras), external fiducial tracking (using high frequency video cameras), internal anatomical marker tracking (using continuous fluoroscopy) etc. At 112, 4D CT images of the target volume are obtained and binned into N phases, where N is an integer. At 114, a motion estimation tool (e.g., DiDIT or any other suitable motion estimation tool) computes motion parameters (e.g., translations, rotations, scale factors, deformable vector fields etc.) for each tracked position of the target volume. At 116, a parameterized set of outputs from the motion estimation tool are stored in a memory or database and is linked to a particular phase N of the 4D CT dataset. This can be performed using timing information from the recorded tracking data and CT images. Other registration techniques can also be used, such as registering the tracking data waveform to an estimate of target motion obtained from CT image analysis. The 4D motion model is populated by monitoring the patient for an extended period of time during simulation, thereby capturing a large number of data points. During this process, a patient is made to perform out-of-the-ordinary tasks (e.g. coughing, deep breathing, shallow breathing etc.) that are rare but may occur during therapy delivery. The simulation phase of the approach thus comprises acts 110, 112, 114, and 116, without being limited thereto.

At 118, a dynamic PTV is generated, during the treatment planning stage. In one embodiment, each set of parameter outputs from the motion estimation tool (e.g., DiDIT) links to a unique phase on the 4D CT dataset (one-to-one mapping). In the case of one-to-one mapping, each output set of the motion estimation tool is assigned a unique PTV that is drawn on the corresponding phase of the 4D CT dataset (see, e.g., FIG. 5). This approach employs a temporally-dense 4D CT data set.

In another embodiment, multiple sets of outputs from the motion estimation tool (e.g., DiDIT) link to a given phase on the 4D CT dataset (many-to-one mapping). In the case of a many-to-one mapping, multiple output sets of the motion estimation tool are assigned a common PTV that is drawn on the phase of the 4D CT dataset to which those outputs correspond (see, e.g., FIG. 6). Under this approach, the 4D CT dataset can be relatively sparse (e.g., 10 phases or some other predetermined number of phases).

At 120, a radiation dose is delivered to a dynamically-changing PTV using real-time tracking information during delivery. In one example, the tracking modality used during the simulation phase is also utilized continuously during treatment delivery (e.g., EM tracking, fluoroscopic movies, etc.). The 4D motion model created during simulation (at 110) and the dynamic PTV generated during the treatment planning stage (at 118) are used to determine which PTV margins to use at which time, based on the real-time analysis of the incoming tracking data in the motion estimation tool. At 122, one or more motion prediction algorithms are executed to predict multi leaf collimator (MLC) leaf positions during delivery. For example, if a patient coughs during treatment delivery, the target volume will deviate from its normal path: the 4D motion model can be used to estimate the positions that will be traversed by the target volume to return to its "normal" or expected path. Based on this information, the appropriate PTV is chosen in advance for those time instants, and the collimator is controlled to deliver radiation to the position of the PTV at a given instant.

It will be understood that the herein-described examples, while relating to radiation therapy, are not limited thereto. Rather, the described systems and methods find application in any therapy planning and/or delivery types, including for example ablation therapy, particle therapy, and the like.

Figure 5:
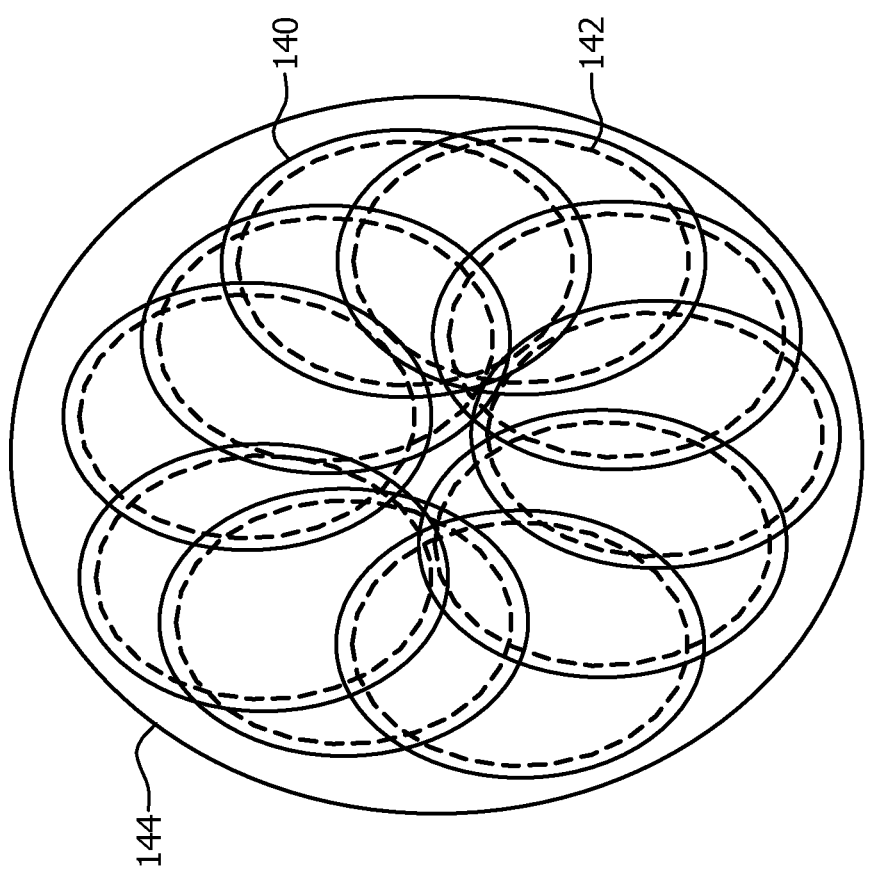
FIG. 5 illustrates a dynamically-changing PTV (solid-line ovals) using real-time tracking, one-to-one mapping to 4D CT phases, and motion prediction to track a target volume (dashed-line ovals) along a trajectory, in accordance with one or more aspects described herein.

FIG. 5 illustrates a dynamically-changing PTV 140 (solid-line ovals) using real-time tracking, one-to-one mapping to 4D CT phases, and motion prediction to track a target volume 142 (dashed-line ovals) along a trajectory, in accordance with one or more aspects described herein. Phases of the target volume motion are then used to control a radiation source and collimator to deliver a radiation dose to the PTV 140 surrounding the target volume 142 at each position or phase along the trajectory, rather than irradiate one large aggregate PTV 144 that encompasses all target volume positions as is conventional. In this manner, radiation dose to healthy tissue surrounding the target volume is reduced.

Figure 6:
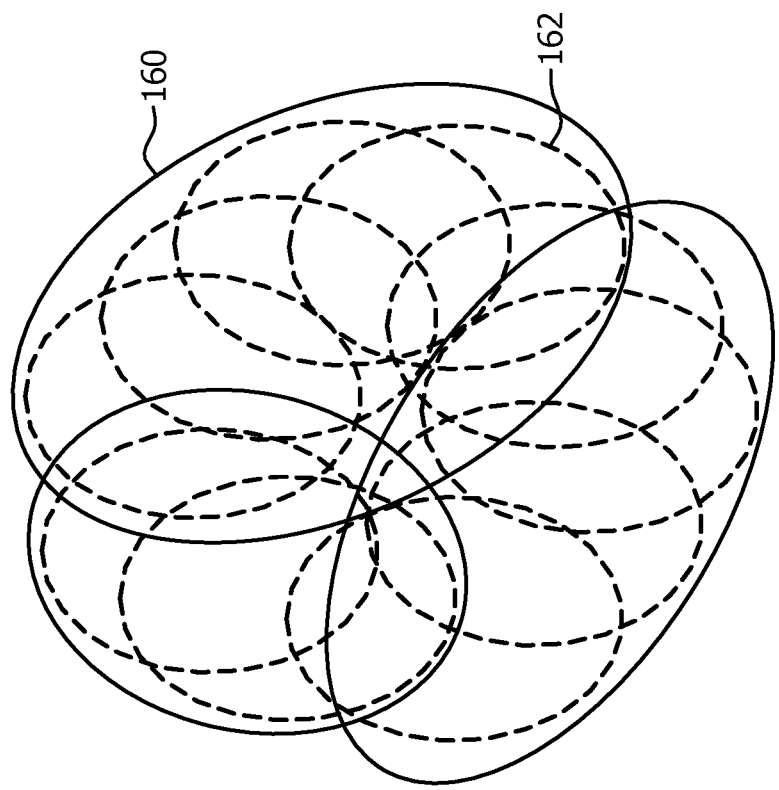
FIG. 6 illustrates a dynamically-changing PTV (solid-line ovals) using real-time tracking, many-to-one mapping to 4D CT phases, and motion prediction, in accordance with one or more aspects described herein.

FIG. 6 illustrates a dynamically-changing PTV 160 (solid-line ovals) using real-time tracking, many-to-one mapping to 4D CT phases, and motion prediction, in accordance with one or more aspects described herein. Phases of the target volume motion are then used to control a radiation source and collimator to deliver a radiation does to the PTV 160 surrounding the target volume 162 (dashed-line ovals) at each position or phase along the trajectory, rather than irradiate one large aggregate PTV that encompasses all target volume positions as is conventional. In this manner, radiation dose to healthy tissue surrounding the target volume is reduced.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A method of reducing radiation dose to healthy tissue near a target volume, comprising:
generating a dynamic planned target volume (PTV) for each of a plurality of motion phases of the target volume identified in a 4D motion model generated by tracking motion of a target volume during computed tomography (CT) data acquisition, wherein the motion phases are identified from one or more CT images reconstructed from acquired CT data;
tracking the target volume; and
at each motion phase of the target volume:
selecting a dynamic PTV corresponding to the motion phase to cover the target volume; and
determining multi-leaf collimator leaf positions and outputting instructions for irradiating the selected dynamic PTV at each motion phase of the target volume.

2. The method according to claim 1, further comprising:
binning the 4D CT images of the target volume in the motion model into N motion phases, where N is an integer greater than 1.

3. The method according to claim 2, further comprising:
computing motion estimation parameters for each tracked position of the target volume.

4. The method according to claim 3, wherein the motion estimation parameters comprise one or more of:
target volume translations;
target volume rotations;
scale factors; and
deformable vector fields.

5. The method according to claim 3, further comprising:
linking, to each of the N motion phases, at least one set of motion estimation parameters.

6. The method according to claim 5, further comprising:
generating and linking a dynamic PTV that covers the target volume in each motion phase using the motion estimation parameters, in order to create a one-to-one mapping of dynamic PTVs to motion phases.

7. The method according to claim 5, further comprising:
generating and linking a dynamic PTV for the target volume across multiple motion phases using the motion estimation parameters, in order to generate a many-to-one mapping of dynamic PTVs to motion phases, wherein at least two dynamic PTVs are generated to cover all motion phases of the target volume.

8. The method according to claim 1, wherein the target volume is tracked using one or more of:
electromagnetic tracking;
surface tracking;
external fiducial tracking; and
internal anatomical marker tracking.

9. The method according to claim 1, wherein the target volume is tracked using optical shape sensing.

10. A non-transitory computer-readable medium having stored thereon computer-executable instructions for performing the method according to claim 1.

11. A therapy planning system that facilitates reducing radiation dose to healthy tissue near a target volume, comprising:
a tracking module that tracks target volume motion using one or more 4D computed tomography (CT) images reconstructed from acquired CT scan data of the target volume;
a processor configured to:
generate a 4D motion model for the target volume using tracking information generated by the tracking module;

generate a dynamic planned target volume (PTV) for each of a plurality of motion phases of the target volume identified in the motion model; and a motion estimation tool configured to track the target volume;

wherein the processor is further configured to, at each motion phase of the target volume:

select a dynamic PTV corresponding to the motion phase to cover the target volume; and determine multi-leaf collimator leaf positions and output instructions for irradiating the selected dynamic PTV at each motion phase of the target volume.

12. The system according to claim 11, wherein the processor is further configured to:

bin the 4D CT images of the target volume in the motion model into N motion phases, where N is an integer greater than 1.

13. The system according to claim 12, wherein the processor is further configured to:

compute motion estimation parameters for each tracked position of the target volume.

14. The system according to claim 13, wherein the motion estimation parameters comprise one or more of:

target volume translations;
target volume rotations;
scale factors; and
deformable vector fields.

15. The system according to claim 13, wherein the processor is further configured to:

link, to each of the N motion phases, at least one set of motion estimation parameters.

16. The system according to claim 15, wherein the processor is further configured to:

generate and link a dynamic PTV that covers the target volume in each motion phase using the motion estimation parameters, in order to create a one-to-one mapping of dynamic PTVs to motion phases.

17. The system according to claim 15, wherein the processor is further configured to:

generate and link a dynamic PTV for the target volume across multiple motion phases using the motion estimation parameters, in order to generate a many-to-one mapping of dynamic PTVs to motion phases, wherein at least two dynamic PTVs are generated to cover all motion phases of the target volume.

18. The system according to claim 11, wherein the tracking module employs one or more of:

electromagnetic tracking;
surface tracking;
external fiducial tracking; and
internal anatomical marker tracking.

19. The system according to claim 11, wherein the tracking module tracks the target volume using optical shape sensing.

20. A method of reducing radiation dose to healthy tissue near a target volume, comprising:

providing tracked target volume position information from a 4D motion model of the target volume to a motion estimation tool;

linking motion parameter information output from the motion estimation tool to motion phases of the target volume indicated by CT scan data;

generating a dynamic planned target volume (PTV) that covers the target volume in each motion phase;

linking the dynamic PTV for each motion phase to tracked motion parameters for each respective motion phase; and determining multi-leaf collimator leaf positions and outputting instructions for irradiating the PTV for each motion phase.

* * * * *